US00PP08772P

United States Patent [19]

Jacobsen

[11] Patent Number: Plant 8,772

[45] Date of Patent: Jun. 7, 1994

[54] POINSETTIA PLANT "490 WHITE"

[75] Inventor: Peter Jacobsen, Skibby, Denmark

[73] Assignee: Paul Ecke Ranch, Inc., Encinitas, Calif.

[21] Appl. No.: 95,104

[22] Filed: Jul. 21, 1993

[51] Int. Cl.[5] ..... A01H 5/00

[52] U.S. Cl. ..... Plt./86.2

[58] Field of Search ..... Plt. 86.2, 86.4

*Primary Examiner*—James R. Feyrer

*Attorney, Agent, or Firm*—Arnold, White & Durkee

[57] ABSTRACT

Poinsettia '490 White' is a new cultivar, distinguished by creamy white bracts and intense dark green foliage with self-branching characteristics. '490 White' is a color sport of the dark red bracted '490' (U.S. Plant Pat. No. 7,825) with the same early flowering response and cultural requirements. The new plant produces a very desirable branched flowering pot plant. The new plant is resistant to epinasty after being confined to shipping containers and recovers rapidly if the plant does become epinastic. The post-production foliage and bract retention is excellent even under low light intensities in the consumer's home.

1 Drawing Sheet

BACKGROUND OF THE NEW PLANT

This new poinsettia cultivar originated as an induced white bracted sport of '490' (U.S. Plant Pat. No. 7,825) in my greenhouse in Skibby, Denmark. It was induced through irradiation of a group of 100 vegetative plants of '490' with 2500 rads of gamma radiation randomly applied to the whole plant. A single plant from the irradiated group exhibited white bracts. The mutant was characterized by its early flowering, self-branching, white flower bracts, and dark green foliage; traits which distinguished it from other poinsettia cultivars on the market and seemed to make it a desirable plant for commercial greenhouse production. No other similar plants were observed from the irradiation nor were any other changes in the group observed which would appear to have commercial merit. '490 White' differed from its parent '490' in having white bracts as compared to the dark red bracts of '490' but otherwise had characteristics similar to the parent. After selection, '490 White' was vegetatively reproduced from stem cuttings for test purposes in Encinitas, Calif. By subjecting clones of this plant to successive generations of vegetative propagation, it was demonstrated that the distinctive characteristics of '490 White' held true from generation to generation.

DESCRIPTION OF THE PHOTOGRAPHS

Poinsettia '490 White' is illustrated in the accompanying color photographs. The upper photo is a side view of a typical branched plant in full flower. The lower photo is a top view of the same plant showing flower and bract formation.

DESCRIPTION OF THE PLANT

The following is a detailed description of this new poinsettia as observed in Encinitas, Calif., U.S.A. during December 1992. Observations were recorded from flowering plants, grown as 3 single stem plants per pot. The pot was 14 cm. in diameter and 11 cm. in height. Color designations are compared to the 1986 edition of R.H.S. Colour Chart, first published in 1966 by The Royal Horticultural Society, London, England.

THE PLANT

Origin: Sport of '490' (U.S. Plant Pat. No. 7,825), induced through irradiation of vegetative plants with 2500 rads of gamma radiation.

Classification:

*Botanic.*—*Euphorbia pulcherrima* Willd.

*Common name.*—Poinsettia.

*Cultivar name.*—'490 White'.

Form: Shrub.

Height: Short.

Growth habit: As a single stemmed plant, upright and short with self-branching side shoots. The application of a chemical growth retardant may not be needed to restrict height for commercial pot plant production. I observed 3 unpinched plants in a pot with an overall height of 36 cm. The bract diameter of individual flowers was 26 cm.

Branching: Axillary branches will develop and termiante in a flower without pinching. However, it is usually desirable to pinch '490 White' and remove all terminal dominance. Then, all axillary branches will develop uniformly and at a faster rate.

Growth rate: Rooting of stem cuttings occurs in 12–18 days under intermittent mist.

Flowering: The plant will flower in about eight weeks under continuous long night conditions and night temperatures of about 16–18 degrees C. Like its parent ('490'), '490 White' will be in full bloom in mid-November in the northern hemisphere under natural daylength conditions. '490 White' flowers earlier than most known poinsettias because flower induction seems to occur in mid-September, about 10 days earlier than normal.

Foliage: At flowering, plants were observed with about 13 uniformly dark green leaves, one leaf per node. The leaves were of medium size, leaf blades typically being 14–15 cm. long and 10–11 cm. wide with leaf petioles 6–7 cm. long. Between the green leaves and the true flower bracts were 4 transitional bracts from the uppermost nodes on each stem. These leaf/bracts were green but changed to white as the flowers matured. At maturity, one or two of these leaf/bracts were neither completely green nor completely white.

*Leaf shape.*—Typical leaves are generally ovate with obtuse bases and acuminate tips. Leaf margins are entire or slightly lobed with 1 or 2 indentations on each side of the leaf blade.

*Color.*—Upper side — Dark green, darker than RHS 139A. Under side — Green, lighter than but near RHS 147A.

Bracts: Generally there were 15–18 white bracts of various sizes subtending the cyathia. The primary bracts have blades typically 14–15 cm. long and 9–10 cm. wide with petioles about 3 cm. long.

*Shape.*—Primary bracts are ovate with acute bases and acuminate tips and weakly lobed with 1 small indentation on either side of the bract. Secondary bracts are elliptic and have entire margins.

*Color.*—Upper side — Creamy White. Near RHS 4D. Under side — Creamy White. Near RHS 4D.

Flowers:

*Cyathia.*—Generally, 16 cyathia (flowers) were present when the plant was in full bloom. Each cyathium was about 6 mm long and 6 mm wide, green in color, and fringed with yellow at the distal end. A yellow nectar cup protrudes from the side of each cyathium. The flower pedicel is also green and about 4 mm in length. The stamens protruding from the cyathia are whitish. The anthers are bifurcate with copious yellow pollen. Cyathia retention was about three weeks beyond the fully mature flower.

*Nectar exudate.*—Present, abundant.

*Seed formation.*—Self-incompatible.

*Fertility.*—Not observed.

Post production: '490 White' is resistant to epinasty after being confined to shipping containers and recovers rapidly if the plant does become epinastic. The foliage and bract retention is excellent even under low light intensities in the consumer's home.

What is claimed is:

1. A new and distinct Poinsettia cultivar, substantially as herein shown and described, distinguished by its intense dark green foliage, white bracts, self branching, early flowering and good leaf and bract retention in the consumer environment.

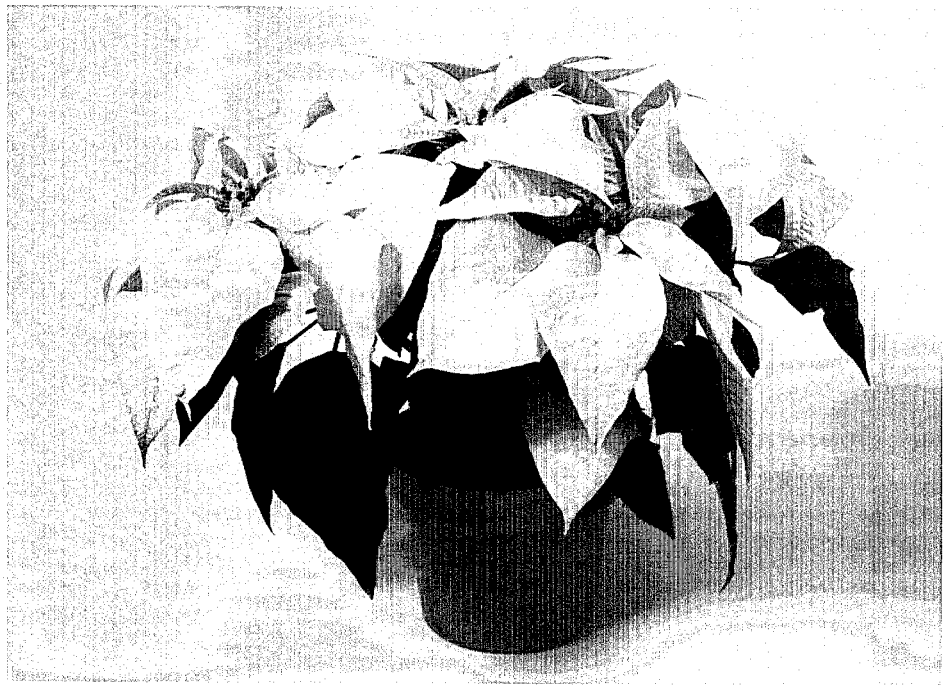
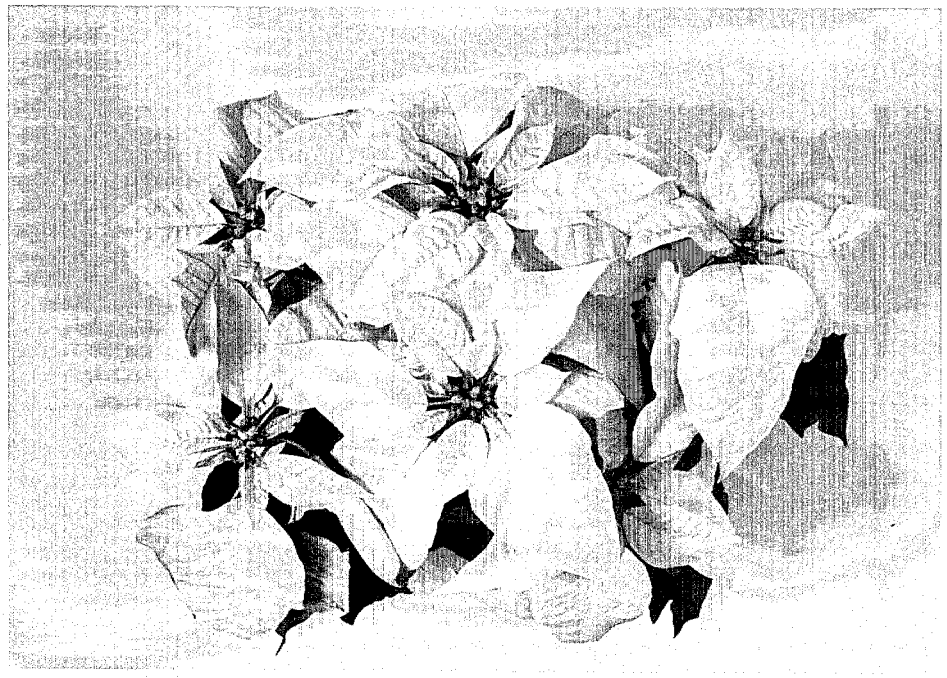

* * * * *